United States Patent [19]

Karakelle et al.

[11] Patent Number: 4,885,077
[45] Date of Patent: Dec. 5, 1989

[54] COMPOSITE MEMBRANE, METHOD FOR ITS PREPARATION AND ELECTROLYTE SENSOR INCLUDING SAME

[75] Inventors: Mutlu Karakelle, Dayton, Ohio; Richard J. Zdrahala, Miami Lakes, Fla.

[73] Assignee: Becton, Dickinson and Company, Franklin Lakes, N.J.

[21] Appl. No.: 272,372

[22] Filed: Nov. 17, 1988

[51] Int. Cl.$^4$ ............................................. G01N 27/40
[52] U.S. Cl. .................................... 204/403; 204/415; 204/418; 204/433; 210/500.27; 210/500.35; 357/25; 422/56; 427/40; 427/41; 427/243; 427/244; 436/163; 436/172
[58] Field of Search ................ 204/418, 403, 433; 427/40, 41, 44, 243, 244; 357/25; 210/500.27, 500.35; 422/56; 436/163, 172

[56] References Cited

U.S. PATENT DOCUMENTS

| Re. 31,879 | 5/1985 | Lübbers et al. | 436/133 |
|---|---|---|---|
| 3,361,587 | 1/1968 | Menikheim et al. | 427/41 X |
| 3,449,154 | 6/1969 | Katz | 427/40 |
| 4,143,949 | 3/1979 | Chen | 427/41 X |
| 4,200,110 | 4/1980 | Peterson et al. | 128/634 |
| 4,505,799 | 3/1985 | Baxter | 204/416 |
| 4,534,356 | 8/1985 | Papadakis | 128/635 |
| 4,536,274 | 8/1985 | Papadakis et al. | 204/433 |
| 4,615,340 | 10/1986 | Cronenberg et al. | 128/635 |
| 4,717,479 | 1/1988 | Itoh et al. | 210/490 |
| 4,776,959 | 10/1988 | Kasai et al. | 210/490 |

FOREIGN PATENT DOCUMENTS

| 209617 | 11/1984 | Japan | 210/500.27 |
|---|---|---|---|
| 2058802A | 4/1981 | United Kingdom | 685/942 |

OTHER PUBLICATIONS

Richard J. Zdrahala et al., pp. 477, 478, The 1987 International Congress on Membranes and Membrane Processes, Tokyo, Japan, Jun. 8–12, 1987.

A Guide to Membrane Separation Technology, Millipore, Laboratory Products Catalogue, p. 24–26.

Primary Examiner—G. L. Kaplan
Attorney, Agent, or Firm—Richard E. Brown

[57] ABSTRACT

A porous composite membrane comprises a base membrane of high mechanical strength and a coating of a hydrophilic polymer on the surface of the membrane and on the walls of the pores. The invention includes a method to prepare the membrane and a biosensor including the membrane.

24 Claims, 1 Drawing Sheet

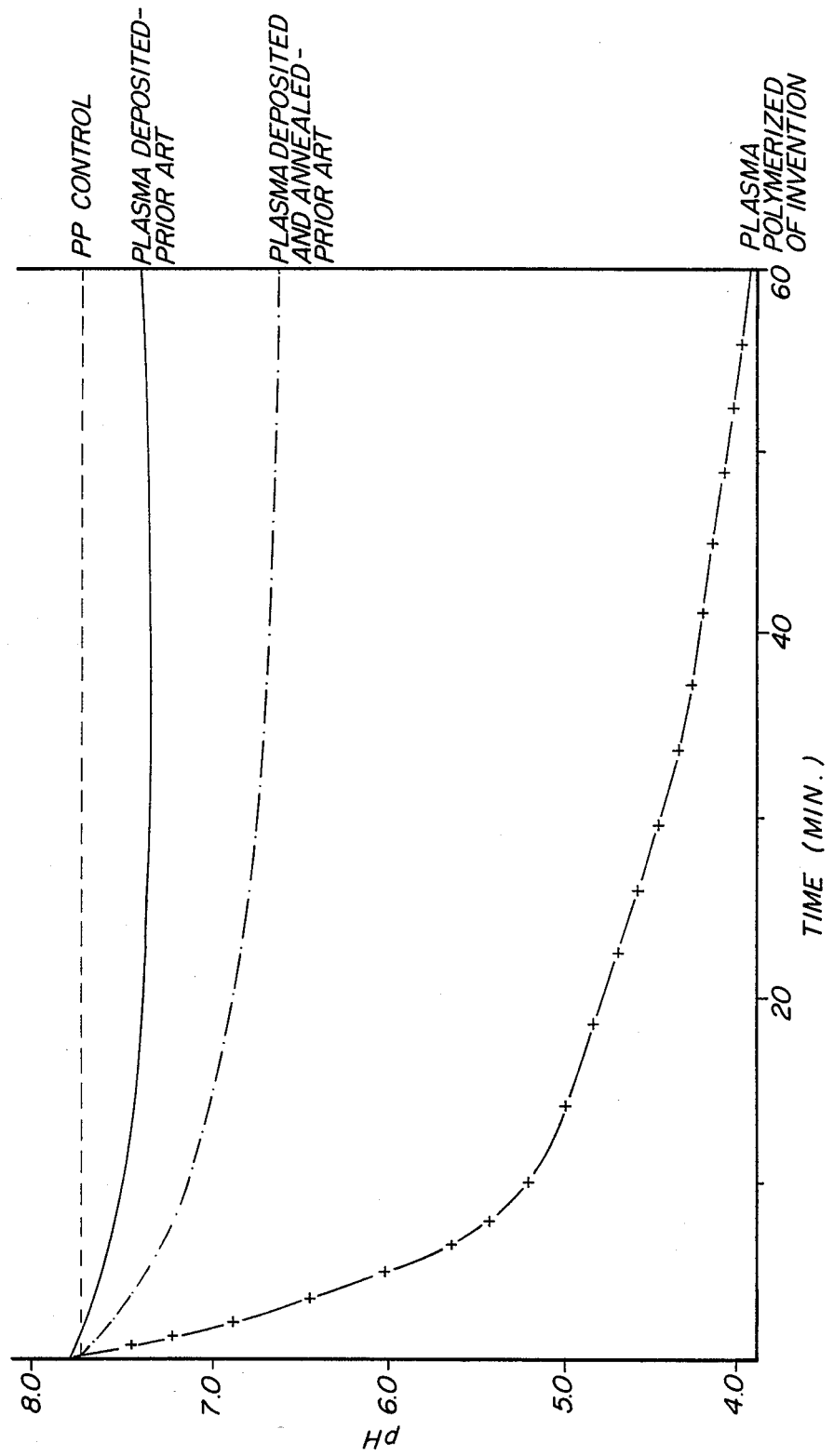

COMPOSITE MEMBRANE, METHOD FOR ITS PREPARATION AND ELECTROLYTE SENSOR INCLUDING SAME

BACKGROUND OF THE INVENTION

1. Field of the Invention.

This invention relates to determination of electrolytes, and more particularly relates to a composite membrane and to an electrolyte sensing device including the membrane useful in making the determination.

2. Background of the Invention

Hydrophilic polymeric membranes are of interest to the industry for numerous applications ranging from extracorporeal blood purification (hemodialysis) to analysis of blood gases and electrolytes. For a typical biomedical application, a suitable hydrophilic membrane should have high ion/solute. permeability, mechanical strength and blood compatibility. Another desirable property, particularly in an analytical medical device application, is dimensional stability of the membrane upon absorption of water.

The ionic permeability of most membranes known in the art depends on their water absorption, which is generally accompanied by swelling. Any significant swelling in turn leads to dimensional changes. These changes represent a significant drawback in applications of the membrane in biosensing devices contemplated for contact with body fluids.

Polypropylene (PP) is a hydrophobic material, non-wettable by water, and thus, even when porous, it is not permeable to ions in an aqueous solution unless a positive pressure gradient is applied. It can be converted to a hydrophilic membrane with excellent dimensional stability and mechanical properties by treatment with surfactants (i.e. Celgard$^R$ 3500, Celanese). The surfactant-treated porous PP, however, is unsuitable for blood and tissue contact applications because the surfactant leaches out of the membrane matrix causing cell lysis.

It is known in the art that plasma surface treatment techniques can be utilized to change the surface energy of polymeric films. A coating of plasma-polymerized ultra thin film changes permanently the surface energy of a substrate without altering bulk properties of the material. Composite membranes based on plasma induced polymerization-deposition of polymer directly onto porous and nonporous substrates have been disclosed by Zdrahala et al. (Abstracts, The 1987 International Congress on Membranes and Membrane Processes, Tokyo, Japan, June 1987. page 477) wherein dimensionally stable hydrophilic membranes are prepared by plasma polymerizing gaseous acrylic acid with concomitant deposition of a layer of polyacrylic acid (PAA) on the PP. These membranes, however, showed only marginal improvement in hydrogen ion diffusion through the disclosed membrane.

Lazear, in GB patent application 2,058,802A discloses a polyolefinic open-celled microporous film rendered hydrophilic by chemically affixing PAA to the pore surfaces. The porous films are limited to those having interconnected pores, commonly referred to as depth filters, and are prepared by coating the pores with acrylic acid and polymerizing with ionizing radiation.

In U.S. Pat. No. 4,717,479, Itoh et al. discloses a porous hydrophilic polyolefin membrane consisting of a hydrophobic polyolefin membrane having surface-grafted thereto a polymerized surface active monomer. The membrane may be of any type, including hollow fiber, planar and tubular types, and the monomer includes a polymerizable olefin group, a hydrophobic group and a hydrophilic group. A method for preparing the membrane includes applying the monomer to the membrane and polymerizing by application of heat or radiation in the presence of a polymerization catalyst.

Sensing devices for determination of blood components are well-known. All such devices utilize a membrane which is permeable to the blood component being analyzed. U.S. Pat. Nos. 4,534,356 and 4.536.274, to Papadakis disclose electrochemical sensors in which membranes useful for blood gas analysis are broadly defined as hydroqels or hydrophilic polymers or copolymers and membranes useful for blood pH determinations are copolymers of fluorine-containing monomers.

A portable assembly for analysis of blood oxygen and carbon dioxide which includes a blood sampler, an electrochemical sensor and blood gas analyzer is disclosed by Cronenberg et al. in U.S. Pat. No. 4,615,340. The sensor includes a gas permeable, ion permeable membrane fabricated of polycarbonate or cellulose and a gas permeable, ion impermeable membrane of polytetrafluoroethylene or PP.

Boold gases are measured by Lübbers et al. in U.S. Pat. No. 31,879 by a fluorescence-based sensor using selective qas permeable membranes and optical fibers to direct incident light to a dye and fluorescence from the dye.

A fiber optic pH probe for physiological studies using an ion permeable cellulose membrane is described by Peterson et al. in U.S. Pat. No. 4,200,110.

Baxter, in U.S. Pat. No. 4,505,799, discloses an ion sensitive field effect transistor (ISFET) for measurement of hydrogen ions which includes a membrane which may be silicon nitride or aluminum oxide.

There is a need for a membrane which combines the high ion permeability of hydrogels with the dimensional stability and meschanical strength of polyolefins. The present invention satisfies this need.

SUMMARY OF THE INVENTION

One aspect of the invention is a composite, hydrophilic, ion permeable membrane which includes a porous polymeric base membrane having a highly crosslinked coating of a hydrophilic polymer thereon. The base membrane of the present invention is of the screen or membrane filter type and consists of a rigid polymeric film having discrete pores (capillaries) therethrough. The coating is on the surface of the membrane and on the walls of the pores. In this disclosure, a coating of hydrophilic polymer on a surface of the membrane and the walls of the pores is referred to as a continuous coating. Preferred base membranes are polyolefins. The most preferred ion permeable membrane of the invention is a porous PP base membrane having thereon a continuous coating of PAA.

Another aspect of the invention is a method for preparing the membrane of the invention. The method includes coating the polymeric base membrane with a monomer of the hydrophilic polymer and plasma-polymerizing the monomer. A preferred method is forming the coating of monomer by steeping the base membrane in a bath of the monomer and polymerizing the monomer by exposing the coating of monomer on the base membrane to a plasma generated from a noble gas.

A third aspect of the present invention is a sensor for a component of a fluid. The sensor includes a sensing element and the membrane of the invention. The preferred sensor is a blood electrolyte sensor in which the sensing element is an ion sensitive field effect transistor. A particularly preferred sensor is a blood pH sensor.

Thus, the invention provides a porous hydrophilic composite membrane which includes a polymeric base membrane, preferably PP, and a continuous coating of hydrophilic polymer thereon. No toxic components, such as surfactants or catalysts are present in the membrane. The coating of hydrophilic polymer does not substantially change the bulk properties and thus the mechanical strength of the PP. Further, minimal absorption of water by the coating of hydrophilic polymer takes place so that substantially no dimensional changes in the composite membrane occur. The membrane is particularly advantageous for use in medical devices in which the membrane comes into contact with body fluids wherein dimensional changes due to swelling and leaching of toxic catalyst molecules are severe disadvantages associated with prior art membranes.

BRIEF DESCRIPTION OF THE DRAWING

The Figure illustrates diffusion of hydrogen ions through the composite membrane of the invention compared to a prior art membrane.

DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiment illustrated and described. The scope of the invention will be measured by the appended claims and their equivalents.

Known blood electrolyte sensors are of three basic types, electrochemical, fiber optic and solid state, and the invention contemplates any known sensor which may be adapted to include the membrane of the invention. Exemplary of, but not limited to, such sensors are electrochemical sensors as described in U.S Pat. Nos. 4,536,274 and 4,615,340; fluorescence sensors as described in U.S. Pat. Nos. 4,200,110 and Re. 31,879; and ISFET sensors as described in U.S. Pat. No. 4,505,799. The disclosures in these patents are herein incorporated by reference.

Sensing assemblies generally include a sensor having a sensing element capable of generating a detectable signal. Exemplary of sensing elements are dyes which fluoresce or change color in the presence of an electrolyte, electrodes which sense changes in potential and solid state transistors which sense a change in the amperage or voltage of an electrical current. Also included in most sensing assemblies are a membrane and apparatus to transmit a signal generated by the element to a data display or analyzer. The membrane generally is selected to be permeable to a substance being sensed but substantially impermeable to substances which may be deleterious to the sensing element or which may interfere with accurate signal generation.

The composite membrane of the present invention combines the hydrophilicity and ion permeability of hydrogels with the physical-mechanical properties of polyolefins, and is particularly suitable for inclusion in sensing assemblies for detection or measurement of water soluble components of a fluid which may diffuse across the membrane. Most preferably, the membrane may be included in a blood analysis assembly. Exemplary of blood components amenable to sensing with the membranes of the invention are gases such as oxygen and carbon dioxide, solutes such as glucose, uric acid, urea and the like, and electrolytes such as ions of hydrogen, potassium, sodium, lithium and chlorine. Preferred components for analysis using the membrane of the invention are blood electrolytes, most preferably, blood hydrogen ions.

Included in the membrane of the invention is a porous polymeric base membrane. Suitable base membranes may be fabricated from, for example, polyurethanes, polyurethaneureas, polystyrene and, preferably, polyolefins, such as PP, polyethylene, and polytetrafluoroethylene. The base membrane may be about 0.01 to 0.1 mm thick and have an effective pore size of about 0.005 to 1.0 $\mu$, preferably about 0.01 to 0.1 $\mu$. Porous polymeric membranes and methods for their production are well-known in the art, and further description of the base membranes is not needed for a full understanding of the invention.

The base membrane, while porous, is hydrophobic and retains its dimensional stability and physical properties in water. Being hydrophobic, it is substantially non-wettable with water and therefore impermeable to water and ions. In accordance with the invention it may be rendered hydrophilic and permeable to ions by applying a continuous coating of a hydrophilic polymer to both the membrane surface and the surfaces of the pores.

Hydrophilic polymers are well known in the art, and any such polymer, which, when applied as a continuous coating renders the base membrane ion permeable, is contemplated to fall within the scope of the invention. Exemplary of, but not limitative of, suitable hydrophilic polymers are polyacrylic acids, polyhydroxyalkyl acrylates, and olefinically substituted lactams. Specific nonlimiting examples of suitable hydrophilic polymers are PAA, polymethacrylic acid, polyhydroxyethyl acrylate and N-vinyl pyrrolidone. The preferred hydrophilic polymer is PAA, an the invention will hereinafter be described in terms of this polymer, although not limited thereto.

Any method of applying a continuous coating of PAA is suitable in accordance with the invention. A preferred method is applying a continuous coating of a monomer of the hydrophilic polymer, i.e., acrylic acid, and polymerizing the applied monomer. It is evident that the acrylic acid may be applied by any conventional technique such as brushing, dipping or spraying. Such methods, while providing some improvement in ion permeability, are less preferred because of difficulty in obtaining complete wetting of narrow lumen walls of the pores with the acrylic acid.

The most preferred method for achieving a continuous coating of PAA is steeping the base membrane in a bath of acrylic acid to form a continuous coating of the monomer and inducing polymerization thereof. The acrylic acid may be dissolved in a solvent, though it is preferred to steep the base membrane neat in the monomer. If it is desired to use a solvent solution of acrylic acid in the steeping process, an organic solvent, such as acetone, is preferred. Although acrylic acid is soluble in water, aqueous solutions of acrylic acid are unsatisfactory because the hydrophobic nature of the PP renders wetting of the pore walls difficult and much less acrylic acid coats the walls.

Steeping may be carried out for any time and at any temperature suitable for achieving a continuous coating. Thus, the temperature of steeping may be from ambient to the softening point of the polymeric base membrane. A preferred temperature range for steeping is from about 40° to 80° C. The time required to obtain a continuous coating of acrylic acid depends on such variables as the temperature of steeping, the pore size, the viscosity of the monomer and the resistance of the base membrane polymeric substrate to wetting by the acrylic acid. While the determination of a suitable time for steeping is well within the purview of one skilled in the art, in general, a steeping time of about 10 minutes to 24 hours is suitable.

After removal of the base membrane from the steeping bath, excess acrylic acid may be removed by any convenient method, such as simply allowing the excess to drip away. The continuous coating of acrylic acid is then ready for polymerization.

In accordance with the invention, polymerization may be performed by inserting the monomer-coated base membrane into a conventional plasma generator and exposing the acrylic acid to a plasma qenerated therein from a gas. Any suitable means for supporting the base membrane in the plasma generator may be used. It is convenient to spread the membrane on a glass plate and place the glass plate between the electrodes of the generator, although other arrangements will be evident to one skilled in the art. The plasma induces polymerization and chain propagation of the acrylic acid so that both sides of the base membrane and the walls of the pores are covered with a continuous coating of PAA.

A preferred plasma generator is a capacitively coupled unit which includes parallel plate electrodes, such as the Plasmatherm$^R$ Model 530 unit, Plasma-Therm, Inc., Kresson, New Jersey. Preferred gases are inorganic gases, such as nitroqen and noble gases such as helium, arqon and neon. Most preferably, the plasma is generated from arqon or helium.

A wide range of power settings, radio frequencies, durations of exposure, temperatures, gas pressures and gas flow rates may be used for plasma generation. Ranges for these parameters which provide advantageous results are power levels of up to 1000 watts, RF frequency of 0.05 to 50 megahertz, 0.01 to 12 hours, 0 to 200° C., 0.1 to 100 torr and 60 to 12,000 cubic centimeters/min. Preferred conditions are power of 15-watts, RF frequency of 13.56 megahertz, 2 minutes, 20° C., 0.2 torr and 100 cubic centimeters/min.

The steeping process of the invention causes acrylic acid molecules to permeate into the PP matrix so that, upon plasma-induced polymerization, PAA molecules are firmly embedded in the PP matrix, thereby providing a substantially permanent bond which prevents leaching and removal of the PAA. The permanently bonded PAA molecules project through the PP surface to provide the hydrophilic surface for water wettability and ion passage. The composite membrane of the invention thus has the form of a modified interpenetrating network (IPN) polymer and is herein referred to as an IPN type polymer.

It is well known that plasma polymerization of a monomer gives a very highly crosslinked polymer, in contrast to thermal polymerization in which no crosslinking occurs in the absence of a crosslinking agent. Thus, because of the hydrophobicity of the base membrane and the crosslinked nature of the coating, the composite membrane of the invention absorbs substantially no water other than that which fills the pores, does not swell to any extent, and does not undergo any dimensional changes in contact with water.

Plasma treatment of a polymeric surface is known to be a surface event. When the layer of acrylic acid coated onto the base membrane of the invention is subjected to the plasma, polymerization on the surface is induced. Although the plasma does not penetrate below the surface of the base membrane and therefore does not reach acrylic acid molecules which have diffused into the PP matrix, the polymerization reaction initiated on the surface propagates and adds these molecules to the growing PAA chain to give the modified IPN type polymer characteristic of the composite membrane of the invention. Further, because the plasma treatment occurs only at the surface, no changes in the bulk properties of the base membrane, such as tensile, modulus and elongation take place, and no degradation of the base membrane is induced, as commonly occurs when polymers are treated with electromagnetic radiation.

The ion permeability of the composite membrane of the invention may be determined, as described in Example III, in a permeability cell having two compartments separated by the membrane of the invention. The result of this experiment is shown in the Figure. It is seen that, after 5 minutes, the pH in the receiving compartment has decreased from 7.5 to 4.5 and after one hour to pH 3.9 due to migration of hydrogen ions through the membrane. In contrast, substantially none of the hydrogen ions passes through the untreated PP base membrane so that no pH change is detected over one hour. A slight pH decrease to about 7.35 occurs with the PP membrane of the prior art (Zdrahala et al. supra.) having a layer of polyacrylic acid resulting from plasma polymerization and deposition of gaseous acrylic acid. It is further seen that, when this prior art membrane is annealed, the pH decreases only to a constant value of 6.6 after one hour.

Diffusion constants (D) for the composite membrane of the invention and the control and prior art membranes were calculated from the ion permeability data using Fick's First Law of Diffusion and are set forth in the Table.

TABLE

| | Membrane | Apparent D(cm$^2$/sec) |
|---|---|---|
| 1. | PP base membrane | nonpermeable |
| 2. | PP base membrane with plasma deposited PAA | 8.1 × 10$^{-11}$ |
| 3. | membrane 2 after annealing | 7.8 × 10$^{-10}$ |
| 4. | composite membrane of Example I | 3.9 × 10$^{-7}$ |

The composite membranes of the invention are translucent when wet and have retained their translucence and surface hydrophilicity over 1.5 years in contact with water thereby supporting the IPN type nature of the membrane matrix having the PAA firmly embedded in the base membrane.

EXAMPLE I

Celgard ® 2500 microporous PP film 25 μ thick with an average effective pore size of 0.04 p was steeped in a bath of acrylic acid at 60° C. for two hours. The film was removed from the bath, excess acrylic acid allowed to drip off, and the film was spread on a glass plate. The plate was placed in the Plasmatherm® Model 530 plasma generator, and the chamber was evacuated. Argon was bled into the chamber over one minute until the qas pressure reached 0.2 torr, and a plasma was generated and maintained at 20° C. for two minutes at 13.56 megahertz 150 watts with an argon flow rate 100 cc/min. The plasma-treated membrane was removed from the chamber and tested for ion permeability in accordance with Example III.

EXAMPLE II

The prior art membrane of drahala et al. (supra) was prepared for comparison purposes as follows:

Celgard200 2500 microporous PP films were placed on the lower electrode of the chamber of the Plasmatherm® Model 530 unit. Acrylic acid vapor was delivered to the chamber from a monomer vessel held at 45° C. while the chamber walls were maintained at 50° C. The acrylic acid was plasma polymerized and deposited on the PP with a plasma generated at a frequency of 50 kilohertz, a power of 220 watts, a chamber pressure of 200 millitorr and a monomer flow rate of 10 cc/min. PAA coatings of varying thickness were obtained by varying the plasma from about 2-15 minutes. Thickness of the PAA coating on these prior art membranes was determined by ellipsometry. Ion permeability was determined in accordance with Example III. These membranes, although having surfaces which were completely water wettable, were only marginally better than the control PP membrane in ion permeability, as shown in the Table and the Figure, because the PAA did not reach the pore walls.

EXAMPLE III

Permeability measurements of the membranes of the invention (Example I) and the prior art (Example II) to hydrogen ions were performed in a two compartment permeability cell which had a membrane test area of 25 $cm^2$ The membranes were converted to their potassium salts by brief immersion into 0.1 KOH solution, then removed from the solution and washed thoroughly with distilled water. Prior to testing, the membranes were equilibrated for two hours at ambient temperature in distilled water. After mounting the membranes into the permeability cell, the cell was placed into a constant temperature bath of 25° C. The receiving compartment of the cell was filled with 275 ml of 5 mM HCl solution and 225 ml of 5 mM NaCl solution was placed into the other compartment. Dry nitrogen gas was used as an inert blanket atmosphere. The pH change in both compartments was measured for 60 minutes using an Orion EA 940 ion analyzer. The apparent diffusion constants were calculated from the obtained data using Fick's First Law of Diffusion.

Thus the invention provides a composite membrane particularly useful as a component of a sensor to be used in contact with body fluids. The composite membrane includes a polymeric base membrane, having discrete pores therethrough, which provides mechanical strength. A coating of a hydrophilic polymer on the membrane surface and the lumen walls of the pores provides water and ion transmission through the pores. The composite membrane is of the modified IPN type so that the coating is firmly adhered to the base polymer without grafting thereby preventing loss of hydrophilicity. The coating is applied to the base polymer by catalyst-free plasma polymerization of the corresponding monomer thereby eliminating the danger of leaching of toxic catalyst into a body fluid. Plasma polymerization also crosslinks the hydrophilic polymer, thereby substantially eliminating uptake of any water into the matrix of the hydrophilic polymer, which is known to cause dimensional changes and reduction in pore size.

What is claimed is:

1. A method for preparing a hydrophilic ion permeable membrane comprising:
   (a) steeping a polyolefinic base screen membrane filter having a pore therethrough in a bath of a monomer of a hydrophilic polymer whereby a coating of said monomer forms on said base membrane and a wall of said pore, and said monomer permeates into, the matrix of said base membrane;
   (b) removing said base membrane having said coating thereon from said bath and
   (c) treating said based membrane having said coating of monomer thereon with a plasma whereby said monomer is polymerized to a crosslinked hydrophilic polymer thereby rendering said membrane hydrophilic and ion permeable.

2. The method of claim 1 wherein said monomer is selected from the group consisting of an unsaturated carboxylic acid, a hydroxyalkyl ester of an unsaturated carboxylic acid and an olefinically unsaturated lactam.

3. The method of claim 2 wherein said unsaturated acid is selected from the group consisting of acrylic acid and methacrylic acid.

4. The method of claim 2 wherein said ester is selected from the group consisting of hydroxyethylmethacrylate and hydroxyethylacrylate.

5. The method of claim 2 wherein said lactam is N-vinyl pyrrolidone.

6. The method of claim 1 wherein said plasma is generated from a gas.

7. The method of claim 6 wherein said gas is a noble gas.

8. A method for preparing a hydrophilic ion
   (a) steeping a polypropylene base screen membrane filter having a pore therethrough in a bath of acrylic acid whereby a coating of said acrylic acid forms on said base membrane and a wall of said pore, and said acrylic acid permeates into the matrix of said base membrane;
   (b) removing said base membrane having said coating thereon from said bath; and
   (c) exposing said base membrane having said coating of acryl polymerizing and crosslinking said acrylic acid so that said membrane is rendered hydrophilic and ion permeable.

9. A hydrophilic ion permeable screen membrane filter comprising a polyolefinic base membrane having a pore therethrough and a coating of an interpenetrating polymeric network type crosslinked hydrophilic polymer on said base membrane and on a wall of said pore, said polymer being selected from the group consisting of polyacrylic acid, polyhy droxyethylacrylate and polyvinylpyrrolidone, said membrane having a hydrogen ion diffusion constant of greater than $7.8 \times 10^{-10}$.

10. The membrane of claim 9 wherein said polyolefin is selected from the group consisting of polyethylene, polypropylenen and polytetrafluoroethylene.

11. The membrane of claim 9 which has a thickness of about 0.01 to 0.1 microns.

12. The membrane of claim 9 wherein the size of said pore is about 0.005 to 1.0 micron.

13. A hydrophilic ion permeable screen membrane filter comprising a polymeric base membrane having a pore therethrough and a coating of an interpenetrating polymeric network type crosslinked hydrophilic polymer on said base membrane and on a wall of said pore, said polymer being selected from the group consisting of polyacrylic acid, polyhydroxyethylacrylate and polyvinylpyrrolidone, said membrane having a hydrogen ion diffusion constant of greater than $7.8 \times 10^{-10}$.

14. A hydrophilic ion permeable screen membrane filter comprising a polypropylene base membrane having a pore therethrough and a coating of an interpenetrating polymeric network type crosslinked polyacrylic acid on said polypropylene membrane and on a wall of said pore, said membrane having a hydrogen ion diffusion constant of greater than $7.8 \times 10^{-10}$.

15. A sensor for blood analysis comprising a sensing element for an electrolyte in a blood stream and a composite membrane having a hydrogen ion diffusion constant of greater than $7.8 \times 10^{-10}$ comprising a polyolefin base screen membrane filter having a pore therethrough and a coating of an interpenetrating polymeric network type crosslinked hydrophilic polymer on said base membrane and on a wall of said pore, said composite membrane being permeable to said electrolyte but impermeable to other components of said blood stream, said sensing element being capable of generating a detectable signal in response to contact with said electrolyte, said polymer being selected from the group consisting of polyacrylic acid, polyhydroxyethylacrylate and polyvinylpyrrolidone.

16. The sensor of claim 15 wherein said sensing element comprises a dye.

17. The sensor of claim 16 wherein said dye is capable of changing color in order to produce a detectable signal.

18. The sensor or claim 16 wherein said dye is capable of emitting fluorescence in order to produce a detectable signal.

19. The sensor of claim 15 wherein said sensing element comprises an electrode.

20. The sensor of claim 15 wherein said electrode is capable of sensing a change in electrical potential in order to produce a detectable signal.

21. The sensor of claim 15 wherein said sensing element is an ion-sensitive solid state transistor.

22. The sensor of claim 21 wherein said is capable of sensing a change in amperage in order to produce a detectable signal.

23. The sensor of claim 21 wherein said transistor is capable of sensing a change in voltage in order to produce a detectable signal.

24. A sensor for blood analysis comprising a sensing element which includes a field effect transistor sensitive to the pH of a blood stream and a composite membrane having a hydrogen ion diffusion constant of greater than $7.8 \times 10^{-10}$ comprising a polypropylene base screen membrane filter having a pore therethrough and a coating of an interpenetrating polymeric network type crosslinked polyacrylic acid on said base membrane and on a wall of said pore, said composite membrane being permeable to hydrogen ions in a blood stream but impermeable to other components of said blood stream, said transistor being capable of generating a detectable signal consequent to contact with said hydrogen ions.

* * * * *